(12) United States Patent
Olson et al.

(10) Patent No.: US 9,290,796 B1
(45) Date of Patent: Mar. 22, 2016

(54) DETECTION OF FOAMING AND BULKING BACTERIA IN WASTEWATER

(75) Inventors: Betty Olson, Trabuco Canyon, CA (US); Pitiporn Asvapathanagul, Norwalk, CA (US)

(73) Assignee: The Regents of the University of California, Oakland, CA (US)

( * ) Notice: Subject to any disclaimer, the term of this patent is extended or adjusted under 35 U.S.C. 154(b) by 442 days.

(21) Appl. No.: 13/452,865

(22) Filed: Apr. 21, 2012

Related U.S. Application Data

(60) Provisional application No. 61/478,390, filed on Apr. 22, 2011.

(51) Int. Cl.
 *C12Q 1/68* (2006.01)
 *C12N 1/20* (2006.01)

(52) U.S. Cl.
 CPC .................................. *C12Q 1/6827* (2013.01)

(58) Field of Classification Search
 None
 See application file for complete search history.

(56) References Cited

PUBLICATIONS

Asvapathanagul, Concurrent Rapid Identification of Bulking and Foaming Bacteria Proceedings of the Water Environment Federation, WEFTEC 2010: Session 11 through Session 20 , pp. 587-600(14) (2010).
Asvapathanagul Concurrent rapid identification of filamentous bacteria using reverse-line blot hybridization Water Environment Laboratory Solutions, vol. 18, No. 1: pp. 5-10 (2011).

*Primary Examiner* — Nancy T Vogel

(57) ABSTRACT

The present invention is directed to the detection of problematic foaming and bulking bacterial species in the biological wastewater treatment process. The invention provides various compositions of matter and methods for the detection of foaming and bulking bacterial species and genera in wastewater and other samples. PCR primers capable of amplifying 16s rRNA gene sequences from various foaming and bulking bacterial species are provided, as are probes that will specifically hybridize with PCR amplification products produced by the disclosed primers. In certain embodiments, the use of the disclosed PCR primers and probes in detection assays is disclosed.

16 Claims, No Drawings

DETECTION OF FOAMING AND BULKING
BACTERIA IN WASTEWATER

CROSS-REFERENCE TO RELATED
APPLICATIONS

This application is based on and claims the benefit of priority of U.S. Provisional Patent Application Ser. No. 61/478,390, filed on Apr. 22, 2011, the contents of which are hereby incorporated by reference

STATEMENT REGARDING FEDERALLY
SPONSORED RESEARCH OR DEVELOPMENT

Not Applicable

REFERENCE TO SEQUENCE LISTING, A
TABLE, OR A COMPUTER PROGRAM LISTING
COMPACT DISK APPENDIX

This application is submitted with a computer readable sequence listing, submitted herewith via EFS as the ASCII text file named: "UCI001SEQLIS_ST25.txt", file size approximately 7155 bytes, created on Apr. 21, 2012 and hereby incorporated by reference in its entirety.

FIELD OF THE INVENTION

This invention relates to the field of microbial identification, specifically the identification of bacterial species within the genera *Mycobacterium, Microthrix, Nocardia, Skermania, Millisia, Tsukamurella, Rhodococcus, Gordonia, Thiothrix* and *Beggiatoa*.

BACKGROUND

The invention relates to detection and identification of foaming and bulking bacteria in order to assess the presence and abundance of these problematic organisms in the biological wastewater treatment processes. Wastewater treatment requires efficient solids separation, which is the separation of treated wastewater (liquid phase) from biomass/bacteria (solid phase). Solids separation problems in the wastewater treatment processes include foaming and bulking. Foaming occurs when specific types of hydrophobic filamentous bacteria overgrow and create foams over the surface area of the treatment equipment, such as the aeration tanks and the secondary clarifiers. Bulking occurs due to the disproportionate growth of specific filamentous bacteria, which detrimentally increases the settling time of the biomass in secondary clarifiers. The occurrence of foaming and bulking can substantially impair treatment plant efficiency. Increased energy and chemical inputs, such as disinfectants, are required to control or eliminate foaming and bulking events. Additionally, these problems result in less effective treatment, as the discharged water often has higher biochemical oxygen demand and total suspended solids, which are negative attributes.

The species which cause foaming and bulking problems have been identified and are known in the art. Foaming is known to be caused by the excessive growth of bacterial species from the genera *Microthrix, Nocardia, Skermania, Millisia, Tsukamurella, Rhodococcus*, and *Gordonia*. Due to their staining properties, these filamentous bacteria may be collectively classified as "acid-fast" bacteria. Bulking is known to be caused several types of filamentous bacteria, some of which are sulfur-oxidizing species from the genera *Thiothrix* and *Beggiatoa*, and herein may be referred to as "sulfur bacteria" or "sulfur species." These foaming and bulking bacterial will herein be collectively referred to as "FBB" for "foaming-bulking bacteria."

While the role of the FBB in foaming and bulking events is known, the study and monitoring of these bacteria is problematic. The presence and abundance of these organisms must be measured in order to (1) understand the operational factors that promote their growth, (2) to assess their abundance and anticipate foaming and bulking events they may cause, (3) to develop effective treatment plant practices and interventions that prevent their growth, and (4) to monitor the efficacy of treatments. Unfortunately, the identification and quantification of these organisms currently requires time-consuming light microscopy analysis, which may be subjective and inaccurate unless supplemented with fluorescence in situ hybridization (FISH) techniques. The use of light microscopy and FISH probes requires expensive equipment, reagents, and highly trained personnel, and is not performed quickly. The expense and required expertise of current FBB identification and quantification methods is generally outside the budget and training of treatment plant personnel.

Thus, there is a need in the art for fast, inexpensive, facile, and accurate methods to assess the presence and abundance of FBB. The inventions described herein fulfill this unmet need.

SUMMARY OF THE INVENTION

The invention provides methods of identifying the presence of FBB genera and species in a sample and quantifying abundance of such FBB. Primers and probes for detecting FBB are provided by the invention, as are kits containing such primers and probes. Methods of the invention can be used to confirm the presence of bacterial species within the genera *Microthrix, Nocardia, Skermania, Millisia, Tsukamurella, Rhodococcus, Gordonia, Thiothrix* and *Beggiatoa*. Methods of the invention also include quantification techniques for measuring the abundance of these FBB.

In one aspect, the invention provides methods of detecting the presence or absence of FBB in a sample, for example a wastewater sample from a wastewater treatment plant. Such methods generally include isolating bacterial DNA from the sample, performing a PCR reaction with such bacterial DNA in the presence of FBB-specific primers, and assaying for the presence of amplification products from the PCR reaction with genera-specific and species-specific probes.

In another aspect, the invention provides methods for quantifying the abundance of FBB species in a sample using quantitative PCR methods. Such methods generally include isolating bacterial DNA from the sample and performing real-time PCR analysis in the presence of FBB-specific primers and genera-specific and species-specific probes.

In another aspect, the invention provides kits for the detection and quantification of FBB. Kits may include FBB-specific primers, FBB probes, combinations thereof, and other materials.

Also provided herein are PCR primers and probes for the amplification and detection of *Mycobacterium* 16s ribosomal RNA. *Mycobacterium* species are non-foaming organisms which are common in wastewater treatment plants, having 16S ribosomal RNA genes sequences which are highly similar to the 16S ribosomal RNA genes of foaming bacteria. *Mycobacterium* probes may be used as a type of non-FBB control to verify the specificity of the FBB probes provided herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the detailed description, and from the claims.

DETAILED DESCRIPTION OF THE INVENTION

As used herein, the following terms will have the definitions set forth below.

A "target polynucleotide," as used herein, refers to a sequence of double stranded DNA or RNA which, if present in a sample, is to be amplified in a PCR reaction. The target polynucleotide is delineated by two flanking sequences, located at the ends of the target polynucleotide.

A "primer" or "PCR primer," as used herein, refers to a short oligonucleotide, for example, between 5 and 35, or 20 and 21 nucleotides in length, which is sufficiently complementary to one strand of a flanking sequence of a target polynucleotide to initiate polymerase activity in a PCR reaction.

A "Primer pair," as used herein, refers to a pairs of primers, one of which is complementary to one of the two flanking sequences of a given target polynucleotide, and the other being complementary to the opposite strand of the second flanking sequence, the primer pairs being of sufficient complementarity to initiate amplification of the target polynucleotide in a PCR reaction.

An "amplicon," as used herein, is an amplified double-stranded polynucleotide which is produced by a target polynucleotide in a PCR reaction containing a primer pair.

FBB Primers and Probes

The invention is based on the identification of novel flanking sequences on the bacterial 16S ribosomal RNA gene of various FBB organisms. One pair of novel flanking sequences is both (1) highly conserved among the acid fast bacteria species and (2) at the same time is unique to these genera and species. Additionally, the intervening target polynucleotides defined by these flanking sequences are variable among many of the acid fast genera and species. Similarly, the inventors have elucidated a pair of flanking sequences conserved within and unique to several species within the sulfur bacteria genus *Thiothrix*, which such flanking sequences delineate an intervening region which is unique to these sulfur species. Additionally, a third set of flanking sequences unique to the sulfur species *Beggiatoa alba* has been identified.

The elucidation of these novel flanking sequences and the target polynucleotides which they define provides the art with valuable tools for the identification of FBB strains. Specifically, the elucidation of the flanking sequences allows the synthesis of complementary primer pairs, which in turn allows the amplification of target polynucleotide sequences. The resulting amplicons, comprising heterogeneous sequences among the various FBB types, may be assayed with novel probes, described herein, which are complementary to and which bind to unique sequences within the amplicons, allowing the detection and differentiation of specific FBB genera and/or species.

The PCR primers of the invention are described in Table 1. One primer pair for amplification of target sequences within the acid-fast bacteria is the AF1 primer pair, comprising SEQ ID 1 and SEQ ID 2 The AF1 primer pair may be used to amplify 16s rRNA gene sequences from various species within the FBB genera *Nocardia*, *Skermania*, *Millisia*, *Rhodococcus*, and *Gordonia*, as well as target sequences within the non-FBB genus *Mycobacterium*. The AF1 forward primer (SEQ ID 1) may also be used in combination with the AF2 reverse primer (SEQ ID 4) to amplify target sequences from various species within the genus *Tsukamurella*. The AF2 forward primer (SEQ ID 3) may be used in combination with the AF1 reverse primer (SEQ ID 2) to amplify target sequences from species within the genus *Microthrix*. The Sul1 primer pair, comprising SEQ ID 5 and SEQ ID 6 may be used to amplify 16s rRNA gene sequences from various species within the genus *Thiothrix*. The Sul2 primer pair, comprising SEQ ID 7 and SEQ ID 8, may be used to amplify 16s rRNA gene sequences from the species *Beggiatoa alba*.

The AF1 forward and reverse primers (SEQ ID 1 and SEQ ID 2) will additionally amplify species from the genera *Bacillus*, *Williamsia* and *Dietzia*, however, these species are rarely found in wastewater in significant concentrations and this cross-amplification of non-FBB species does not generally limit the accuracy of the FBB detection assays described herein.

TABLE 1

Primer Sequences. Character codes are standard WIPO ST.25 Codes, with "A" denoting adenine; "T" denoting thymine, "C" denoting cytosine, "G" denoting guanine, "Y" denoting a pyrimidine (either T or C), "R" denoting a purine (either A or G), "N" denoting any base (either A, T, C, or G), and "M" denoting an amino base (either A or C).

| Primer Name | SEQ ID | Sequence (5'-3') |
|---|---|---|
| AF1 (forward) | 1 | ACT NGA GTA CTA YAG GGG AG |
| AF1 (reverse) | 2 | ACA GGA CAR GGG TTG CGC TC |
| AF2 (forward) | 3 | ACT AGA GTC CGG TAG GGG AG |
| AF2 (reverse) | 4 | ATA AGA TAA GGG TTG CGC TC |
| Sul1 (forward) | 5 | GCT AGA RTG TGG GAG AGG RA |
| Sul1 (reverse) | 6 | TRC CTC AGC GTC ART GTT G |
| Sul2 (forward) | 7 | ATA CTG CTK AGM TAG AGT AC |
| Sul 2 (reverse) | 8 | TAC CTC AGY GTC AGT ATC A |

The probes of the invention comprise nucleotide sequences which bind selectively to various amplicons produced by the primer pairs describe above. Some probes are species-specific, others will bind to amplicons from a range of species within a single FBB genus. Table 2 describes the various probes of the invention.

TABLE 2

Probes. This table lists nucleotide sequences for various probes of the invention. "Probe Name" denotes probe identifier; "SEQ ID" denotes corresponding nucleotide sequence identifier; "Sequence" is the probe's nucleotide sequence, listed 5' to 3'; "Primer Pair" denotes the primer pair(s) which produce amplicons to which the probe will hybridize; "Genus Specificity" denotes the genus from which one or more species will produce amplicons that each probe selectively hybridizes with.

| Probe Name | SEQ ID | Sequence (5'-3') | Primer Pair | Genus Specificity |
|---|---|---|---|---|
| Mill | 9 | ACA CCG GAC GCT GGT AGA GAT ATC AGT TCC | AF1(forward) AF1(reverse) | Millisia |
| Sker | 10 | ACA CCA GAC GCT GGT AGA GAT ATC AGT TCC | AF1(forward) AF1(reverse) | Skermania |
| Noc | 11 | ACA CCG GAA ACC TGC AGA GAT GTA GGC CCC | AF1(forward) AF1(reverse) | Nocardia |
| Tsuk | 12 | TTG ACA TAT AGA GGA TCG CCG | AF1(forward) AF2(reverse) | Tsukamurella. |
| Gor1 | 13 | GGG TAC TAG GTG TGG GGC TCA TTT CAC GAG | AF1(forward) AF1(reverse) | Gordonia |
| Gor2 | 14 | GGT AGT AAC TGA CGC TGA GGA GCG AAA GCG | AF1(forward) AF1(reverse) | Gordonia |
| Rho1 | 15 | CGG AAA GCC GTA GAG ATA CSG CCC CCC TTG | AF1(forward) AF1(reverse) | Rhodococcus |
| Rho2 | 16 | GTA CCG GAC GAC TGC AGAGAT GTG GTT TCC | AF1(forward) AF1(reverse) | Rhodococcus |
| Rho3 | 17 | CGG AAA GCT GCA GAG ATG TGG CCC CCC TTG | AF1(forward) AF1(reverse) | Rhodococcus |
| Myc1 | 18 | GGG TTT CCT TCC TTG GGA TC | AF1(forward) AF1(reverse) | Mycobacterium |
| Myc2 | 19 | GGG TTT CCT TCC TTT AGG GAT | AF1(forward) AF1(reverse) | Mycobacterium |
| Myc3 | 20 | GGT TCC TTC CTT GGG ATC C | AF1(forward) AF1(reverse) | Mycobacterium |
| Mic | 21 | GAG AAC TCA ACT CTC TCC GCG CCG TAG CTA | AF2(forward) AF1(reverse) | Microthrix |
| Beg1 | 22 | CCA CGC CCT AAA CGA TGA GAA YTA GAT GTT | Sul2(forward) Sul2(reverse) | Beggiatoa |
| Beg2 | 23 | CCA CGC CCT AAA CGA TGA GAA YTA GCT GTT | Sul2(forward) Sul2(reverse) | Beggiatoa |
| Thio | 24 | ATA GAG ATC GGA AGG AAC AYC AGT GGC GAA | Sul1(forward) Sul1(reverse) | Thiothrix |

The Mill probe (SEQ ID 9) has 100% homology to 16s rRNA gene sequences in the species *Millisia brevia*.

The Sker probe (SEQ ID 10) has 100% homology to 16s rRNA gene sequences in the species *Skermania piniformis*.

The Noc probe (SEQ ID 11) has 100% homology to 16s rRNA gene sequences in the species *Nocardia abscessus, Nocardia brasilensis, Nocardia farcinica, Nocardia levis, Nocardia polyresistens, Nocardia soli/terrovolcana, Nocardia alba, Nocardia brevicatena, Nocardia flavorosea, Nocardia lijiangensis, Nocardia pseudobrasilensis, Nocardia speluncae, Nocardia araoensis, Nocardia carnea, Nocardia fluminea, Nocardia neocaledoniensis, Nocardia pufis, Nocardia takedensis, Nocardia arthritidis, Nocardia cummidelens, Nocardia gamkensis, Nocardia ninae, Nocardia rhamnosiphila, Nocardia tenerifensis, Nocardia asiatica, Nocardia cyriacigeorgica, Nocardia harenosa, Nocardia novocastrensa, Nocardia salmonicida, Nocardia testacea, Nocardia devorans, Nocardia higoensis, Nocardia paucivorans, Nocardia shimofusensis, Nocardia thailandica, Nocardia beijingensis, Nocardia exalbida, Nocardia jinanensis, Nocardia pigrifrangens, Nocardia sienata*, and *Nocardia xishanensis*. The Noc probe (SEQ ID 11) also has 100% homology to 16s rRNA gene sequences within some strains of *Nocardia asteroids*.

The Tsuk probe (SEQ ID 12) has 100% homology to 16s rRNA gene sequences within all species in the genus *Tsukamurella*.

The Gor1 probe (SEQ ID 13) has 100% homology to 16s rRNA gene sequences within the species *Gordonia alkanivorans, Gordonia amicalis, Gordonia australis, Gordonia bronchialis, Gordonia cholesterolivorans, Gordonia desulfuricans, Gordonia hydrophobica, Gordonia malaquae, Gordonia namibiensis, Gordonia neofelifaecis, Gordonia nitida, Gordonia rubripertinctu, Gordonia shandongensis, Gordonia sihwensis, Gordonia spumae*, and *Gordonia westfalica*.

The Gor2 probe (SEQ ID 14) has 100% homology to 16s rRNA gene sequences within the species *Gordonia amarae, Gordonia aichiensis, Gordonia alkanivorans, Gordonia amicalis, Gordonia bronchialis, Gordonia cholesterolivorans, Gordonia desulfuricans, Gordonia effusa, Gordonia hirsuta, Gordonia jacobaea, Gordonia lacunae, Gordonia malaquae, Gordonia namibiensis, Gordonia neofelifaecis, Gordonia nitida, Gordonia otitidis, Gordonia paraffinivorans, Gordonia polyisoprenivorans, Gordonia rhizosphera, Gordonia rubripertinctus, Gordonia shandongensis, Gordonia sihwensis, Gordonia sinesedis, Gordonia soli, Gordonia spumae, Gordonia sputi*, and *Gordonia terrae*.

The Rho1 probe (SEQ ID 15) has 100% homology to 16s rRNA gene sequences within the species *Rhodococcus corynebacterioides, Rhodococcus equi, Rhodococcus erythropolis, Rhodococcus fascians, Rhodococcus globerulus, Rhodococcus imtechensis, Rhodococcus jostii, Rhodococcus luteus, Rhodococcus koreensis, Rhodococcus kroppenstedtii, Rhodococcus kunmingensis, Rhodococcus opacus, Rhodococcus percolates, Rhodococcus triatomae, Rhodococcus tukisamuensis, Rhodococcus wratislaviensis*, and *Rhodococcus percolates*.

The Rho2 probe (SEQ ID 16) has 100% homology to 16s rRNA gene sequences within the species *Rhodococcus rhodochrous, Rhodococcus pyridinivorans*, and *Rhodococcus gordonia*.

The Rho3 probe (SEQ ID 17) has 100% homology to 16s rRNA gene sequences within the species *Rhodococcus baikonurensis, Rhodococcus boritolerans, Rhodococcus erythreus, Rhodococcus erythropolis, Rhodococcus marinonascens, Rhodococcu .opacus, Rhodococcus qingshengii*, and *Rhodococcus ruber*.

The Mic probe (SEQ ID 21) has 100% homology to 16s rRNA gene sequences within the species *Candidatus 'Microthrix parvicella.'*

The Beg1 probe (SEQ ID 22) and the Beg2 probe (SEQ ID 23) have 100% homology to 16s rRNA gene sequences within the species *Beggiatoa alba*.

The Thio probe (SEQ ID 24) has 100% homology to 16s rRNA gene sequences within the species *Thiothrix caldifontis, Thiothrix disciformis, Thiothrix eikelboomi, Thiothrix flexilis, Thiothrix lacustris, Thiothrix nivea, Thiothrix ramose*, and *Thiothrix unzii*.

The probes having 100% homology to 16s rRNA gene sequences within a given species will, under stringent conditions, as known in the art, hybridize specifically with amplicons from those species. Under less stringent conditions, the probes will hybridize with species having 16s rRNA gene sequences with less than 100% sequence identity to the probe sequences. For example, amplicons from species having sequences between 70% to 99% sequence identity to a given probe may hybridize to that probe, depending on the stringency of the hybridization reaction. Adjusting the stringency of the hybridization reaction is within the skill of one in the art, for example, the stringency of the hybridization may be lowered by lowering the temperature of the washing step in a hybridization assay or by increasing the ratio of SSPE to SDS in the washing solution mixture. Accordingly, running the hybridization reactions of the invention at lower stringency allows for the detection of the presence of closely related species, subspecies, and variants of the species listed above.

Some embodiments of the invention encompass kits, comprising various combinations of the nucleotide sequences disclosed herein. For example, in one embodiment, the invention comprises a kit containing the two primers of the AF1 primer pair (having the nucleotide sequences of SEQ ID 1 and SEQ ID 2). In another exemplary embodiment, the invention comprises a kit comprising the two primers of the AF1 primer pair (having the nucleotide sequences of SEQ ID 1 and SEQ ID 2) and the AF2 forward (SEQ ID 3) and reverse primer (SEQ ID 4). In another exemplary embodiment, the invention comprises a kit comprising the two primers of the Sul1 primer pair (having the nucleotide sequences of SEQ ID 5 and SEQ ID 6). In another exemplary embodiment, the invention comprises a kit comprising the two primers of the Sul2 primer pair (having the nucleotide sequences of SEQ ID 7 and SEQ ID 8). In another exemplary embodiment, the invention comprises a kit comprising all FBB PCR primers (SEQ ID 1, SEQ ID 2, SEQ ID 3, SEQ ID 4, SEQ ID 5, SEQ ID 6, SEQ ID 7, and SEQ ID 8. In another exemplary embodiment, the invention comprises a kit comprising two or more of the probes listed in Table 2. For example, in one exemplary embodiment the invention comprises a kit comprising at least two of the following probes: the Mic probe (SEQ ID 21), the Noc probe (SEQ ID 11), the Sker probe (SEQ ID 10), the Mill probe (SEQ ID 19), the Tsuk probe (SEQ ID 12), the Rho1 probe (SEQ ID 15), the Rho2 probe (SEQ ID 16), the Rho 3 probe (SEQ ID 17), the Gor1 probe (SEQ ID 13) the Gor2 probe (SEQ ID 14), the Thio probe (SEQ ID 24), the Beg1 probe (SEQ ID 22), and the Beg 2 probe (SEQ ID 23). at least one probe from Table 2 specific for species from the genus *Rhodococcus* (selected from the group consisting of SEQ ID 15, SEQ ID 16, or SEQ ID 17), at least one probe from Table 2 specific for species from the genus *Gordonia* (selected from the group consisting of SEQ ID 13 or SEQ ID 14), at least one probe from Table 2 specific for species from the genus *Thiothrix* and at least one probe from Table 2 specific for species from the genus *Beggiatoa* (selected from the group consisting of SEQ ID 23 or SEQ ID 24). Optionally, the kits of the invention may comprise at least one probe for species from the genus *Mycobacterium* (selected from the group consisting of SEQ ID 18, SEQ ID 19, or SEQ ID 20). In another embodiment, the invention comprises a kit comprising at least one pair of primers, for example AF1 forward (SEQ ID 1) and AF1 reverse (SEQ ID 2), AF1 forward (SEQ ID 1) and AF2 reverse (SEQ ID 4), AF2 forward (SEQ ID 3) and AF1 reverse (SEQ ID 2), Sul1 forward (SEQ ID 5) and Sul1 reverse (SEQ ID 6), Sul2 forward (SEQ ID 7) and Sul2 reverse (SEQ ID 8) selected from Table 1 and one or more of the probes listed in Table 2.

The primers and probes of the invention may be synthesized by any means known in the art for the production of nucleotide sequences. Automated methods for the facile generation of oligonucleotides and longer sequences are well known in the art. The synthesis of primers and probes is readily carried out by any number of commercial suppliers. If labeled probes are desired, these may be labeled using any number of means known in the art, for example end-labeling, nick translation labeling, random primer labeling methods, and other labeling techniques compatible with the selected synthesis method, as known in the art. PCR primers may also be labeled, in order to generate labeled amplicons, for example, PCR primers labeled with cyanine dyes may be used, as may biotinylated PCR primers, resulting in a biotinylated amplification product to which labels may be conjugated.

One of skill in the art will understand that effective variants of the sequences disclosed herein may be substituted for the disclosed sequences. An effective variant of a sequence comprises a modified version of the sequence (e.g., truncation, addition, or nucleotide substitution) which such modified sequence retains some or all of its functions (e.g. a modified primer sequence which facilitates the amplification of at least some of the same target sequences amplified by the unmodified primer). For example, the complements of the disclosed probe sequences may be used. Truncated version of the primer and probe sequences disclosed herein may also be used effectively. For example, truncated versions of the disclosed primers, for example of 13 to 19 bases in length, may be utilized. Likewise, truncated versions of the disclosed probe sequences, ranging in length from 8 to 19 bases may be utilized. Additionally, it will be understood by one of skill in the art that effective primer pairs and probes based on the sequences disclosed herein may be made by slightly shifting the coordinates of the target sequences, either upstream or downstream from the regions complementary to the disclosed primers and probes. Lastly, it will be understood that various nucleotide substitutions may be made within the sequences disclosed. Complementarity between primers and probes and their target sequences need not be perfect and stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

It is also understood by one of skill in the art that various nucleotide analogs, modified nucleotides, and other compositions may be substituted for the DNA sequences disclosed herein, including equivalent RNA sequences, as well as modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

Assays for the Identification of FBB in a Sample

The primer pairs and probes described above may be used in various assays to determine the presence of FBB in a sample. The basic method for the identification assay comprises the following process:
1. a sample is collected which putatively contains FBB bacteria
2. bacterial DNA is extracted from the sample;
3. a PCR reaction is run, containing the bacterial DNA and a pair of PCR primers capable of amplifying 16s rRNA gene sequences from at least one FBB species;
4. if any amplification product is produced, the amplification product is denatured and exposed to an appropriate FBB probe under hybridizing conditions; and
5. if hybridization between the FBB probe and the amplification product is detected, this indicates that the genera or species corresponding to that FBB probe is/are present in the sample.

The samples of the invention comprise any material putatively containing FBB bacteria. For example, water, foam, or solids from a wastewater treatment plant, at any phase of the treatment process may be used. Such samples are expected to contain many species of bacteria. Samples from cultured bacteria, including mixed cultures, may also be used.

Bacterial DNA may be isolated from the sample by any means known in the art for the separation of DNA from bacterial cells. Methods of isolating bacterial DNA from wastewater samples are known in the art, for example, as described in Yu, and Mohn, Killing two birds with one stone: simultaneous extraction of DNA and RNA from activated sludge biomass, *Canadian Journal of Microbiology*, 45(3), 269-272 (1999). Wang et al., Improving PCR and qPCR detection of hydrogenase A (hydA) associated with Clostridia in pure cultures and environmental sludges using bovine serum albumin, *Applied Microbiology and Biotechnology*, 77(3), 645-656 (2007). Any sample preparation may be utilized which yields extracted DNA that is amenable to PCR.

It will be understood by one of skill in the art that in an alternative embodiment, RNA may be extracted from the bacterial cells and utilized in the subsequent PCR reactions. For example, mRNA may be extracted and put into a PCR reaction directly, as known in the art. Alternatively, bacterial RNA may be converted to DNA via standard reverse transcriptase methods known in the art.

The bacterial DNA (or cDNA or RNA) samples are put into a PCR reaction with one or more pairs of PCR primers capable of amplifying FBB 16s rRNA gene sequences, in sufficient amounts for the amplification of target polynucleotides, if present. PCR methods are well known in the art, for example as described in PCR Troubleshooting and Optimization: The Essential Guide, Kennedy and Oswald (ed.s), Caister Academic Press (2011), and PCR Basics, McPherson and Moller, Taylor and Francis (New York) (2006). PCR methodology, reagents, and devices vary widely, and it is within the skill of one in the art to determine the proper conditions for an effective amplification reaction, for example, the sufficient concentration of a given primer pair, enzyme selections and amounts, temperature conditions, the number of cycles required, and the proper preparation of bacterial DNA samples.

Upon completion of the PCR reaction, if at least one species targeted by the FBB primers used in the reaction was present in the sample, an amplification product should be present. If more than one FBB species targeted by the FBB primers was present in the sample, the resulting amplification product will consist of a mixture of amplicons representing the various species that were present.

The PCR amplification process of the invention may be carried out using various combinations of primers. For example, the AF1 primer pair (SEQ ID 1 and SEQ ID 2) may be used ("PCR Reaction 1"). Alternatively, the AF1 forward primer (SEQ ID 1) may be used in combination with the AF2 reverse primer (SEQ ID 4) ("PCR Reaction 2"). Alternatively, the AF2 forward primer (SEQ ID 3) may be used in combination with the AF1 reverse primer (SEQ ID 2) ("PCR Reaction 3"). Alternatively, the Sul1 primer pair (comprising SEQ ID 5 and SEQ ID 6) may be used ("PCR Reaction 4"). Alternatively, the Sul2 primer pair (comprising SEQ ID 7 and SEQ ID 8) ("PCR Reaction 5") Due to the similar annealing temperatures of the primer sequences disclosed herein, multiple primer pairs may be utilized in a single PCR reaction. For example, in some embodiments, the AF1 forward primer (SEQ ID 1), the AF1 reverse primer (SEQ ID 2), the AF2 forward primer (SEQ ID 3) and the AF2 reverse primer (SEQ ID 4) may be used in a single PCR reaction that will amplify target sequences from all acid fast FBB species, as well as *Mycobacterium* species. In another embodiment, all the acid fast primers (SEQ ID 1, SEQ ID 2, SEQ ID 3, SEQ ID 4) are included in a PCR reaction in addition to one or both of sulfur species primer pairs, e.g., the Sul1 primer pair (comprising SEQ ID 5 and SEQ ID 6) and/or the Sul2 primer pair (comprising SEQ ID 7 and SEQ ID 8). Alternatively. In a preferred embodiment, a single PCR reaction including all the PCR primers of Table 1 (SEQ ID 1, SEQ ID 2, SEQ ID 3, SEQ ID 4, SEQ ID 5, SEQ ID 6, SEQ ID 7 and SEQ ID 8) is run), providing a single step reaction that can amplify target sequences from all FBB genera, if present in the sample. In an alternative preferred embodiment, PCR Reaction 1, PCR Reaction 2, PCR Reaction 3, PCR Reaction 4, and PCR Reaction 5, are run separately, resulting in the amplification of target sequences from all FBB genera, if present in the sample.

In the next step, the amplification product is then assayed with least one appropriate probe. An appropriate probe is a probe which will hybridize to an amplicon produced by a specific primer pair. For example, if the AF1 primer pair (SEQ ID 1 and SEQ ID 2) was used in the PCR reaction, any of probes listed in Table 2 that will hybridize to amplicons produced by the AF1 primer pair would be an appropriate probe, for example, the Mill probe (SEQ ID 9), the Sker probe (SEQ ID 10), the Noc probe (SEQ ID 11), the Gor1 probe (SEQ ID 13), the Gor2 probe (SEQ ID 14), the Rho1 probe (SEQ ID 15), the Rho 2 probe (SEQ ID 16), or the Rho3 probe (SEQ ID 17). If the AF1 forward primer is used in combination with the AF2 reverse primer, the Tsuk probe (SEQ ID 12) would be an appropriate probe. If a PCR reaction is performed using the AF2 forward primer (SEQ ID 3) in combination with the AF1 reverse primer (SEQ ID 2), the Mic probe would be an appropriate probe. If a PCR reaction is performed using the Sul1 primer pair (SEQ ID 5 and SEQ ID 6), the Thio probe (SEQ ID 24) would be an appropriate probe. If a PCR reaction is performed using the Sul2 primer pair (SEQ ID 7 and SEQ ID 8), the Beg1 probe (SEQ ID 22) and/or Beg2 probe (SEQ ID 23) would be an appropriate probe.

A hybridization assay is performed using the amplification product from the PCR reaction and the selected probe(s). If hybridization is detected between the probe and PCR amplification product, this indicates that at least one species specific to that probe (as described above) was present in the sample.

Assaying for hybridization may be accomplished using any number of diverse methods known in the art of molecular biology. Exemplary assay methods and tools include Southern blots, microarrays, capillary gel electrophoresis, dot-blot assays, reverse dot-blot assays, surface Plasmon resonance assays, magnetic bead hybridization assays, microfluidic DNA hybridization assays, and any other method known in the art for the detection of hybridization between two nucleotide sequences. Exemplary commercially available assays include NimblGen™ (Roche), Cantilever Sensor™ (Concentris), HYBD-1 Hybridization Kit (Sigma), and Photoprobe™ (Vector Laboratories). Such assays and methods are well known and widely used within the art of molecular biology, and the skilled practitioner may readily adapt such protocols to the methods and compositions disclosed herein.

Preferred hybridization assays allow the simultaneous assay of multiple probes. For example, assays in which multiple probes are immobilized on a solid surface at specifically addressed locations are especially amenable to the methods of the invention. In such assay methods, the amplification products of the PCR reaction are labeled by various means, while unlabeled probes are immobilized in discreet patches on a surface such as nylon, nitrocellulose, glass, or other surface which can bind single stranded DNA, for example by FMOC conjugation, avidin-biotin mediated conjugation, etc., as known in the art. For example, positively charged nylon membranes may be used, to which denatured probes may be fixed. Alternatively, probes may be 5'-amino modified and then adhered to a negatively charged nylon membrane, for example a Biodyne C membrane (Pall Corporation). The immobilized probes are then exposed to a solution containing the denatured amplification product (from a PCR reaction run using appropriate PCR primers for such probe), and if amplicons specific to a probe are present in the solution, they will bind with the immobilized probes. The amplification product solution is then washed away, and only those labeled amplicons that have hybridized with the probes will remain, creating a detectable signal at the known location in which a patch of a specific probe has been immobilized. Exemplary assays include mircroarrays and reverse dot blot assays. Reverse dot blot assay methods are well known in the art, for example, as described in Fiss et al., DNA Amplification and Reverse Dot Blot Hybridization for Detection and Identification of Mycobacteria to the Species Level in the Clinical Laboratory, J Clin. Microbiol. 30: 1220-1224 (1992), Ehrman et al., Reverse dot blot hybridization: A useful method for the direct identification of lactic acid bacteria in fermented food, FEMS Microbiol Lett 117:143-149 (1994); Xing et al., Rapid detection of intestinal pathogens in fecal samples by an improved reverse dot blot method, World J Gastroenterol. 15(20): 2537-2545 (2009); Asvapathanagul et al., Concurrent Rapid Identification of Bulking and Foaming Bacteria, Proceedings of the Water Environment Federation, WEFTEC 2010: Session 11 through Session 20, pp. 587-600(14) (2010); and Asvapathanagul et al., Concurrent rapid identification of filamentous bacteria using reverse-line blot hybridization, Water Environment Laboratory Solutions, Volume 18, Number 1: pp 5-10 (2011). Any method of labeling the amplification product may be utilized, including fluorescent labeling, chemoluminescent labeling, radioactive labeling, quantum dot labeling, dual label systems, etc., as known in the art. In some embodiments, both the probes and the PCR amplification product are labeled, for example in dual label colormetric systems. Non-radioactive labeling systems are preferred, for example chemiluminescent labels such as the CDP Star™ system (Amersham).

Chemiluminescent and fluorescent assays are generally qualitative, i.e. they are able to detect the presence of a given FBB species in a sample. However, the intensity of the hybridization signal will often vary with the relative abundance of the organism being detected. Accordingly, methods such as the reverse line blot method may also provide semi-quantitative measurement of species abundance in a sample.

Qualitative assays may also be adapted for quantification using most probable number analysis. In such assays, a sample is serially diluted and the dilutions are separately assayed for presence or absence of the target organism. The dilution factor at which signal disappears is used to estimate the concentration of the amplicon in the original solution. Multiple replicates may be used at or around the critical dilution in order to increase the resolution of the assay. Exemplary most probable number assays for the quantification of microbes include Hesselsoe et al., Quantification of ammonia oxidizing bacteria in soil using microcolony technique combined with fluorescence in situ hybridization (MCFU-FISH), FEMS Microbiol. Ecology 38:87-95 (2001), Vester and Ingvorsen, Improved Most-Probable-Number Method To Detect Sulfate-Reducing Bacteria with Natural Media and a Radiotracer, Appl. Environ. Microbiol. 64 (5): 1700-1707 (1998), and Fredslund et al., Development and Application of a Most-Probable-Number-PCR Assay To Quantify Flagellate Populations in Soil Samples, Appl. Environ. Microbiol. April 2001 vol. 67 no. 4 1613-1618. In adapting the qualitative assays of the present invention to most probable number analysis, two methods may be applied. First, the starting bacterial DNA sample may be diluted, and the dilutions included in a series of PCR reaction, followed by probe hybridization experiments to determine presence or absence. Alternatively, a single PCR reaction may be run and the resulting amplification product solution serially diluted and these dilutions subjected to a series of hybridization assays to determine presence or absence.

Quantitative FBB Detection Methods

Using the primer pairs and probes disclosed herein, various quantitative PCR (qPCR) methods may be used to provide a quantitative measure of FBB abundance in a sample. Numerous quantitative PCR equipment and methods are known in the art and may be readily applied. Exemplary fluorescent labeling systems for qPCR, for example using TaqMan™ (Applied Biosystems), Prime Time™ (Integrated DNA Technologies), or other qPCR reagents known in the art. For example, the PCR conditions, reagents and protocols from Example 2 may be adapted for qPCR detection of FBB species.

In some embodiments, quantitative PCR may be applied after less expensive qualitative or semi-quantitative assays, as described above, have been applied to a sample and have confirmed the presence of one or more FBB types. In such cases, only the appropriate primers and/or probes complementary to the identified FBB types are used, reducing the expense of the procedure.

EXAMPLES

Example 1

Isolation of Bacterial DNA from Wastewater

DNA was extracted from 1 mL wastewater collected from wastewater treatment plants using the modified bead beating protocol, as described in Yu, and Mohn, Killing two birds with one stone: simultaneous extraction of DNA and RNA from activated sludge biomass, *Canadian Journal of Microbiology*, 45(3), 269-272 (1999), Wang et al., Improving PCR and qPCR detection of hydrogenase A (hydA) associated with Clostridia in pure cultures and environmental sludges using bovine serum albumin, *Applied Microbiology and Biotechnology*, 77(3), 645-656 (2007), and Huang et al., (2010). "Influence of physicochemical and operational parameters on *Nitrobacter* and *Nitrospira* communities in an aerobic activated sludge bioreactor." *Water Research*, 44(15), 4351-4358. DNA was extracted from three subsamples of each sample. Cell lysis was achieved using cell disruption by Fast-Prep®-24 (MP Biomedicals™, Irvine, Calif.) with 1.5 g of 0.1 mm glass disruption beads (rpi, Mount Prospect, Ill.) in 1 mL volume of DNA extraction buffer (50 mM Tris-HCl pH 8.0 (FISHER Scientific, Fairlawn, N.J.), 5 mM EDTA (FISHER Scientific, Fairlawn, N.J.), and 3% sodium dodecyl sulfate (FISHER Scientific, Fairlawn, N.J.)) added to sludge pellet. After the first bead-beating, a 600 µL volume of supernatant was transferred to a new 2 mL tube, another 600 µL, of DNA extraction buffer was added to the original bead beating tube and the above process was repeated. The second 600 µL volume of supernatant was then transferred to another 2 mL tube. Ammonium Acetate (FISHER Scientific, Fairlawn, N.J.) was then added into the 600 µL solution to obtain 2 M final concentration and the solutions were left on ice for 10 min. The DNA extracts were each washed with a 500 µL volume of phenol/chloroform/isoamyl alcohol (25:24:1) (FISHER Scientific, Fairlawn, N.J.) followed by a 500 µl volume of chloroform (FISHER Scientific, Fairlawn, N.J.). After DNA purification, a 600 µL volume of isopropanol (FISHER Scientific, Fairlawn, N.J.) was added for DNA precipitation at −20° C. for an hour, after which the DNA was washed again with 70% ethanol (FISHER Scientific, Fairlawn, N.J.) and air dried. A 50 µL volume of HPLC grade sterile water (FISHER Scientific, Fairlawn, N.J.) was added to the DNA. Then, the DNA extracts from first and second bead beading were combined. DNA was diluted 1:10 to determine concentration and purity using DU® 7400 spectrophotometer (BECKMAN, Orange, Calif.). The purity ($A_{260}/A_{280}$) ranged between 1.60-1.80. HPLC grade sterile water (FISHER Scientific, Fairlawn, N.J.) was used to dilute wastewater extracts. These samples were prepared into 1:50 dilution for future analysis. The diluted and undiluted DNA samples were immediately stored until use at −80° C.

Example 2

PCR Amplification of Target Sequences

PCR reactions are performed using a GeneAmp® PCR System 2700 (Applied Biosystems, Calif.) with a 5-minute holding at 94° C., 20 s of denaturing at 94° C., and 40 s of annealing at 51.2° C. (representing the annealing temperature of the AF1 forward primer, the lowest annealing temperature of the FBB PCR primers) for each of 35 cycles, followed by a 7-minute final extension at 72° C. Then, amplified samples are cooled to 4° C. and then stored at −50° C. until hybridization assays are performed. The master mixture for PCR is composed of 1× buffer with 2 mM of magnesium chloride, 250 µM of deoxyribonucleotide triphosphate, 0.5 units of AmpliTaq DNA polymerase, and 10 pM of each primer from the selected primer pair(s). The mixture is then brought to a final volume of 20 µL with high-performance liquid-chromatography water, to which 5 µL of each sample DNA extract solution, as prepared in Example 1, is added. Average DNA yields produced by the reaction range from 2-20 ng.

Example 3

Reverse Line Blot Assay

Using the methods of Example 1 and 2, bacterial DNA is isolated from a wastewater sample and subjected to a single PCR reaction, utilizing all eight primers in Table 1 and utilizing biotinylated versions of the eight primers in 10 pM concentration. Biotinylated primers may be obtained from commercial suppliers (e.g. Sigma Genosys) or synthesized according to methods known in the art. The resulting amplification product mixture will contain biotinylated amplicons from the any of the following FBB genera, *Microthrix, Nocardia, Skermania, Millisia, Tsukamurella, Rhodococcus, Gordonia, Thiothrix* and *Beggiatoa*, if present in the original sample.

The Mill, Sker, Noc, Gor1, Gor2, Tusk, Rho1, Rho2, Rho3, Mic, Beg1, Beg2, and Thio probes are synthesized. Probes may be obtained from commercial custom oligonucleotide suppliers, or may be synthesized according to methods known the art. Probes are then amino-modified on the 5' end, using methods known in the art.

The reverse line blot assay is carried out on a negatively charged nylon membrane. A Biodyne C™ (Pall Corporation) 14.2 cm×14.2 cm membrane is incubated in 16% EDAC (N-(3-Dimethylaminopropyl)-N'-ethylcarbodiimide hydrochloride) in 0.1M MES (pH 4.5) for 15 minutes to activate carboxyl groups on membrane. Then, the solution is removed from the membrane. The membrane is rinsed with distilled water for 1 minute, then the membrane is placed in a Miniblotter® 45 (Immunetics, Boston, Mass.). The excess liquid is removed from the membrane in the miniblotter using a vacuum.

Meanwhile, the amino group modified oligonucleotide probe is diluted in 0.5M $NaHCO_3$ (pH 8.4) to obtain the final volume of 145 µL with 100-500 pmole of probe. Then, the probe solution for each type of probe is added into separate slots in the miniblotter and incubated at room temperature for 70 minutes. After the excess probe solution is removed from the miniblotter slots using vacuum, the membrane is transferred from the miniblotter to a glass tray containing 100 mL of 0.1 M NaOH for 9 minutes to inactivate carboxyl groups on the membrane surface. Then, the membrane is transferred into a tray containing 100 mL of 60° C. preheated a 2×SSPE and 0.1% SDS solution (pH 7.4) at 60° C. for 5 minutes. Then, the membrane is sealed and stored at 20° C. until use.

Prior to hybridization, the membrane is soaked in a shaking tray for 5 minutes in a 2× saline-sodium phosphate-EDTA (SSPE) buffer with 0.1% sodium dodecyl sulfate (SDS).

While the membrane is immersed, 10 µL of PCR product mix is mixed with 10 µL of denaturation solution and incubated for 5 minutes at room temperature. Then, 125 µL of 2×SSPE with 0.1% SDS is added to the same tube. This mixture is left at room temperature until hybridization is performed.

The membrane is placed in a Miniblotter® 45 (Immunetics, Boston, Mass.). All remaining liquid in the Miniblotter® 45 is removed by vacuum. Next, 125 ul of denatured PCR product mix is added onto each slot in the miniblotter. The membrane hybridization is performed at 50° C. for 30 minutes in the HB-3B hybridizer (Techne, Staffordshire, England).

Afterward, the membrane is washed twice in washing solution (2×SSPE, 0.5% SDS) at 61.4° C. for 10 minutes before being transferred again to the HB-3B hybridizer. The membrane is incubated with 1:2000 of diluted streptavidin-conjugated alkaline phosphatase in washing solution at room temperature for 30 minutes in the hybridizer. The membrane is then washed twice with TBS (pH7.5) at room temperature for 5 minutes. Then, the membrane is incubated with 1:50 dilution of NBT/BCIP in TBS (pH9.5) for 7-8 minutes before the membrane is rinsed with distilled water to stop the colorimetric reaction and air dry.

The membrane then is then incubated in CDP-Star Detection Reagent ($C_{18}H_{19}C_{12}O_7PNa_2$; Amersharm Biosciences, GE Healthcare, Buckinghamshire, England) for 4 minutes at room temperature. The membrane is removed from the solution with forceps, marked so that the probe and PCR product side can be identified, and placed between two transparent Xerox sheets. Afterward, it is put into a cassette. In the darkroom, the film (Amersharm Hyperfilm ECL™) is placed on the clear Xerox sheet on the marked side of the membrane. The film is exposed for 60 minutes.

A hybridization signal on the blot for any given probe is indicative of the presence, in the original wastewater sample, of that/those species having 16s rRNA gene sequences to which the probe will hybridize.

What is claimed is:

1. A method of identifying the presence of a wastewater bacterial type in a sample, comprising the following steps:
   isolating bacterial DNA from the sample;
   performing a PCR amplification reaction which includes the bacterial DNA and PCR primers comprising SEQ ID 1 and SEQ ID 2;
   collecting the amplification product from the PCR amplification reaction and incubating it, under hybridizing conditions, with one or more wastewater bacterial identification probes; and
   assaying for the hybridization of the one or more wastewater bacterial identification probes to the amplification product,
   wherein the detectable hybridization of a wastewater bacterial identification probe to an amplification product is indicative of the presence of that probe's corresponding wastewater bacterial type being present in the sample.

2. The method of claim 1, wherein the sample is water from a wastewater treatment plant.

3. The method of claim 1, wherein
   the one or more wastewater bacterial identification probes comprises SEQ ID 9, wherein detectable hybridization between this probe and the PCR amplification product is indicative of the presence of *Millisia brevia* in the sample.

4. The method of claim 1, wherein
   the one or more wastewater bacterial identification probes comprises SEQ ID 10, wherein detectable hybridization between this probe and the PCR amplification product is indicative of the presence of *Skermania piniformis* in the sample.

5. The method of claim 1, wherein
   the one or more wastewater bacterial identification probes comprises SEQ ID 11, wherein detectable hybridization between this probe and the PCR amplification product is indicative of the presence of at least one species of the genus *Nocardia* in the sample.

6. The method of claim 1, wherein
   the one or more wastewater bacterial identification probes comprises SEQ ID 13, wherein detectable hybridization between this probe and the PCR amplification product is indicative of the presence of at least one species of the genus *Gordonia* in the sample.

7. The method of claim 1, wherein
   the one or more wastewater bacterial identification probes comprises SEQ ID 14, wherein detectable hybridization between this probe and the PCR amplification product is indicative of the presence of at least one species of the genus *Gordonia* in the sample.

8. The method of claim 1, wherein
   the PCR amplification products are labeled; and
   the one or more wastewater bacterial identification probes is immobilized on a solid surface.

9. The method of claim 1, wherein
   the PCR amplification products are biotinylated;
   the one or more wastewater bacterial identification probes is immobilized on a solid surface in discreet patches comprising a single probe type; and
   the detection of hybridization is carried out by contacting the probe-bound amplicons with a strepavidin-conjugated label and observing a signal from the label.

10. The method of claim 1, wherein
    the PCR amplification product is immobilized on a solid surface in discreet patches;
    the one or more wastewater bacterial identification probes is labeled; and
    the hybridization process is carried out by contacting each of the discreet patches of immobilized PCR amplification product with a solution containing a single probe type.

11. The method of claim 1, wherein
    the one or more wastewater bacterial identification probes comprises SEQ ID 15, wherein detectable hybridization between this probe and the PCR amplification product is indicative of the presence of at least one species of the genus *Rhodococcus* in the sample.

12. The method of claim 1, wherein
    the one or more wastewater bacterial identification probes comprises SEQ ID 16, wherein detectable hybridization between this probe and the PCR amplification product is indicative of the presence of at least one species of the genus *Rhodococcus* in the sample.

13. The method of claim 1, wherein
    the one or more wastewater bacterial identification probes comprises SEQ ID 17, wherein detectable hybridization between this probe and the PCR amplification product is indicative of the presence of at least one species of the genus *Rhodococcus* in the sample.

14. The method of claim 1, wherein
    the one or more wastewater bacterial identification probes comprises SEQ ID 18, wherein detectable hybridization between this probe and the PCR amplification product is indicative of the presence of at least one species of the genus *Mycobacterium* in the sample.

15. The method of claim 1, wherein
    the one or more wastewater bacterial identification probes comprises SEQ ID 19, wherein detectable hybridization between this probe and the PCR amplification product is indicative of the presence of at least one species of the genus *Mycobacterium* in the sample.

16. The method of claim 1, wherein
    the one or more wastewater bacterial identification probes comprises SEQ ID 20, wherein detectable hybridization between this probe and the PCR amplification product is indicative of the presence of at least one species of the genus *Mycobacterium* in the sample.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Consensus PCR primer sequence for amplifying
      16s rRNA gene sequences, derived from bacterial genera: Millisia
      spp., Skermania spp., Nocardia spp., Tsukamurella spp., Gordonia
      spp., Rhodococcus spp., and Mycobacterium spp.
<220> FEATURE:
<221> NAME/KEY: misc_feature
<222> LOCATION: (4)..(4)
<223> OTHER INFORMATION: n is a, c, g, or t

<400> SEQUENCE: 1
actngagtac tayaggggag                                            20

<210> SEQ ID NO 2
<211> LENGTH: 20
<212> TYPE: DNA
<213> ORGANISM: Artificial Sequence
<220> FEATURE:
<223> OTHER INFORMATION: Consensus PCR primer sequence for amplification
      of 16s rRNA gene sequences, derived from the following bacterial
      genera: Millisia spp., Skermania spp., Nocardia spp., Gordonia
      spp., Rhodococcus spp., Mycobacterium spp., and Microthrix spp

<400> SEQUENCE: 2
acaggacarg ggttgcgctc                                            20

<210> SEQ ID NO 3
<211> LENGTH: 20
<212> TYPE: DNA
<213> ORGANISM: Artificial Sequence
<220> FEATURE:
<223> OTHER INFORMATION: Consensus PCR primer sequence for the
      amplification of 16s rRNA gene sequences, derived from bacterial
      species within the genus Microthrix spp.

<400> SEQUENCE: 3
actagagtcc ggtaggggag                                            20

<210> SEQ ID NO 4
<211> LENGTH: 20
<212> TYPE: DNA
<213> ORGANISM: Artificial Sequence
<220> FEATURE:
<223> OTHER INFORMATION: Consensus PCR primer sequence for amplificaiton
      of 16s rRNA gene sequences, derived from species in the genus
      Tsukamurella spp.

<400> SEQUENCE: 4
ataagataag ggttgcgctc                                            20

<210> SEQ ID NO 5
<211> LENGTH: 20
<212> TYPE: DNA
<213> ORGANISM: Artificial Sequence
<220> FEATURE:
<223> OTHER INFORMATION: Consensus PCR primer sequence for amplification
      of 16s rRNA gene sequences, derived from species in the genus
      Thiothrix spp.

<400> SEQUENCE: 5
gctagartgt gggagaggra                                            20

```
<210> SEQ ID NO 6
<211> LENGTH: 19
<212> TYPE: DNA
<213> ORGANISM: Artificial Sequence
<220> FEATURE:
<223> OTHER INFORMATION: Consensus PCR primer sequence for amplification
      of 16s rRNA gene sequences, derived from species in the genus
      Thiothrix spp.

<400> SEQUENCE: 6
trcctcagcg tcartgttg                                                    19

<210> SEQ ID NO 7
<211> LENGTH: 20
<212> TYPE: DNA
<213> ORGANISM: Artificial Sequence
<220> FEATURE:
<223> OTHER INFORMATION: Consensus PCR primer sequence for amplification
      of 16s rRNA gene sequences, derived from species in the genus
      Beggiatoa

<400> SEQUENCE: 7
atactgctka gmtagagtac                                                   20

<210> SEQ ID NO 8
<211> LENGTH: 19
<212> TYPE: DNA
<213> ORGANISM: Artificial Sequence
<220> FEATURE:
<223> OTHER INFORMATION: Consensus PCR primer sequence for amplification
      of 16s rRNA gene sequences, derived from species in the genus
      Beggiatoa

<400> SEQUENCE: 8
tacctcagyg tcagtatca                                                    19

<210> SEQ ID NO 9
<211> LENGTH: 30
<212> TYPE: DNA
<213> ORGANISM: Millisia brevia

<400> SEQUENCE: 9
acaccggacg ctggtagaga tatcagttcc                                        30

<210> SEQ ID NO 10
<211> LENGTH: 30
<212> TYPE: DNA
<213> ORGANISM: Skermania piniformis

<400> SEQUENCE: 10
acaccagacg ctggtagaga tatcagttcc                                        30

<210> SEQ ID NO 11
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species within the
      genus Nocardia spp.

<400> SEQUENCE: 11
acaccggaaa cctgcagaga tgtaggcccc                                        30

<210> SEQ ID NO 12
<211> LENGTH: 21
<212> TYPE: DNA
```

```
<213> ORGANISM: Artificial Sequence
<220> FEATURE:
<223> OTHER INFORMATION: Consensus sequence for the detection of 16s
      rRNA gene sequences, derived from multiple species within the
      genus Tsukamurella

<400> SEQUENCE: 12
ttgacatata gaggatcgcc g                                             21

<210> SEQ ID NO 13
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Gordonia spp.

<400> SEQUENCE: 13
gggtactagg tgtggggctc atttcacgag                                    30

<210> SEQ ID NO 14
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Gordonia spp.

<400> SEQUENCE: 14
ggtagtaact gacgctgagg agcgaaagcg                                    30

<210> SEQ ID NO 15
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Rhodococcus spp.

<400> SEQUENCE: 15
cggaaagccg tagagatacs gccccccttg                                    30

<210> SEQ ID NO 16
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Rhodococcus spp.

<400> SEQUENCE: 16
gtaccggacg actgcagaga tgtggtttcc                                    30

<210> SEQ ID NO 17
<211> LENGTH: 30
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Rhodococcus spp.

<400> SEQUENCE: 17
cggaaagctg cagagatgtg gccccccttg                                    30
```

<210> SEQ ID NO 18
<211> LENGTH: 20
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Mycobacterium spp.

<400> SEQUENCE: 18
gggtttcctt ccttgggatc                                              20

<210> SEQ ID NO 19
<211> LENGTH: 21
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Mycobacterium spp.

<400> SEQUENCE: 19
gggtttcctt cctttaggga t                                            21

<210> SEQ ID NO 20
<211> LENGTH: 19
<212> TYPE: DNA
<213> ORGANISM: Artificial Sequence
<220> FEATURE:
<223> OTHER INFORMATION: Consensus sequence for the detection of 16s
      rRNA gene sequences, derived from multiple species in the genus
      Mycobacterium spp.

<400> SEQUENCE: 20
ggttccttcc ttgggatcc                                               19

<210> SEQ ID NO 21
<211> LENGTH: 15
<212> TYPE: DNA
<213> ORGANISM: Candidatus Microthrix parvicella

<400> SEQUENCE: 21
gagaactcaa ctctc                                                   15

<210> SEQ ID NO 22
<211> LENGTH: 30
<212> TYPE: DNA
<213> ORGANISM: Beggiatoa alba

<400> SEQUENCE: 22
ccacgcccta aacgatgaga aytagatgtt                                   30

<210> SEQ ID NO 23
<211> LENGTH: 30
<212> TYPE: DNA
<213> ORGANISM: Beggiatoa alba

<400> SEQUENCE: 23
ccacgcccta aacgatgaga aytagctgtt                                   30

<210> SEQ ID NO 24
<211> LENGTH: 30
<212> TYPE: DNA
<213> ORGANISM: Artificial Sequence
<220> FEATURE:

```
<223> OTHER INFORMATION: Consensus sequence for the detection of 16s
      rRNA gene sequences, derived from multiple species in the genus
      Thiothrix spp.

<400> SEQUENCE: 24
atagagatcg gaaggaacay cagtggcgaa                                          30
```